(12) United States Patent
Krebs

(10) Patent No.: US 7,861,717 B1
(45) Date of Patent: Jan. 4, 2011

(54) CONTROLLED GAS-SUPPLY SYSTEM

(75) Inventor: Christian Krebs, Vienna (AT)

(73) Assignee: INO Therapeutics GmbH (AT)

( * ) Notice: Subject to any disclaimer, the term of this patent is extended or adjusted under 35 U.S.C. 154(b) by 888 days.

(21) Appl. No.: 10/737,431

(22) Filed: Dec. 16, 2003

Related U.S. Application Data

(63) Continuation-in-part of application No. 09/341,975, filed on Aug. 26, 1999, now abandoned.

(51) Int. Cl.
F16K 31/02 (2006.01)
A62B 7/04 (2006.01)
A61M 15/08 (2006.01)
A61M 16/00 (2006.01)

(52) U.S. Cl. .............. 128/204.23; 128/204.26; 128/204.21; 128/203.22; 128/203.25

(58) Field of Classification Search ............ 128/204.26, 128/204.21, 204.23, 203.22, 203.25
See application file for complete search history.

(56) References Cited

U.S. PATENT DOCUMENTS

| | | | |
|---|---|---|---|
| 4,262,686 A | | 4/1981 | Heim et al. |
| 4,281,651 A | * | 8/1981 | Cox ................. 128/204.23 |
| 4,526,188 A | | 7/1985 | Olsson et al. |
| 4,686,974 A | * | 8/1987 | Sato et al. ........... 128/204.23 |
| 4,686,975 A | | 8/1987 | Naimon et al. |
| 4,798,689 A | | 1/1989 | Heim et al. |
| 4,832,014 A | | 5/1989 | Perkins |
| 4,877,023 A | * | 10/1989 | Zalkin ................. 128/204.21 |
| 4,928,684 A | | 5/1990 | Breitenfelder et al. |
| 4,932,401 A | * | 6/1990 | Perkins ................. 128/203.12 |
| 4,932,402 A | | 6/1990 | Snook et al. |
| 4,971,049 A | | 11/1990 | Rotariu et al. |
| 5,094,235 A | | 3/1992 | Westenskiw et al. |
| 5,195,528 A | | 3/1993 | Hok |
| 5,370,112 A | | 12/1994 | Perkins |
| 5,396,882 A | | 3/1995 | Zapol |
| 5,404,871 A | | 4/1995 | Goodman |
| 5,411,059 A | | 5/1995 | Sever et al. |
| 5,423,313 A | | 6/1995 | Olsson et al. |
| 5,558,083 A | * | 9/1996 | Bathe et al. ............ 128/203.12 |
| 5,720,278 A | * | 2/1998 | Lachmann et al. ..... 128/204.23 |
| 5,735,268 A | | 4/1998 | Chua et al. |

(Continued)

FOREIGN PATENT DOCUMENTS

DE 34 16 291 A 3/1985

(Continued)

OTHER PUBLICATIONS

"Inhaled Nitric Oxide: A Selective Pulmonary Vasodilator Reversing Hypoxic Pulmonary Vasoconstriction", by Frostell et al.; Circulation (1991); 83: 2038-2047.

*Primary Examiner*—Patricia M Bianco
*Assistant Examiner*—Nihir Patel
(74) *Attorney, Agent, or Firm*—Connolly Bove Lodge & Hutz

(57) ABSTRACT

The invention relates to a gas-supply system for patients receiving artificial respiration or breathing spontaneously, in which one or several gases (for example NO, oxygen) are added to the respiration gas at varying proportions (continuously or intermittently) by means of a control device (program control, sensor control or combined program/sensor control). This gas-supply system allows for adaptive dosing of the gas to suit individual patients.

22 Claims, 4 Drawing Sheets

U.S. PATENT DOCUMENTS

| | | |
|---|---|---|
| 5,738,090 A | 4/1998 | Lachmann et al. |
| 5,752,509 A | 5/1998 | Lachmann et al. |
| 5,839,433 A | 11/1998 | Higenbottam |
| 5,845,633 A | 12/1998 | Psaros |
| 5,890,490 A | 4/1999 | Aylsworth et al. |
| 5,918,596 A * | 7/1999 | Heinonen ............ 128/204.21 |
| 6,032,665 A | 3/2000 | Psaros |
| 6,116,240 A | 9/2000 | Merrick et al. |
| 6,125,846 A * | 10/2000 | Bathe et al. ............ 128/202.22 |
| 6,155,256 A * | 12/2000 | Wallin .................. 128/203.16 |
| 6,269,811 B1 | 8/2001 | Duff et al. |
| 6,581,599 B1 * | 6/2003 | Stenzler ................ 128/204.23 |

FOREIGN PATENT DOCUMENTS

| | | |
|---|---|---|
| DE | 37 08 146 A | 9/1988 |
| DE | 37 12 598 | 10/1988 |
| DE | 43 25 319 C | 4/1994 |
| DE | 43-09 923 A | 9/1994 |
| DE | 43 17 730 C | 3/1995 |
| EP | 0 354 388 A | 7/1989 |
| EP | 0 413 555 A | 2/1991 |
| GB | 2 170 731 A | 8/1985 |
| WO | WO-A-90 04425 | 5/1990 |
| WO | WO-A-91 14476 | 10/1991 |
| WO | WO-A-92 10228 | 6/1992 |
| WO | WO-A-92 11052 | 7/1992 |

* cited by examiner

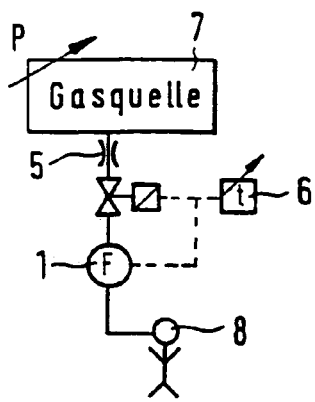
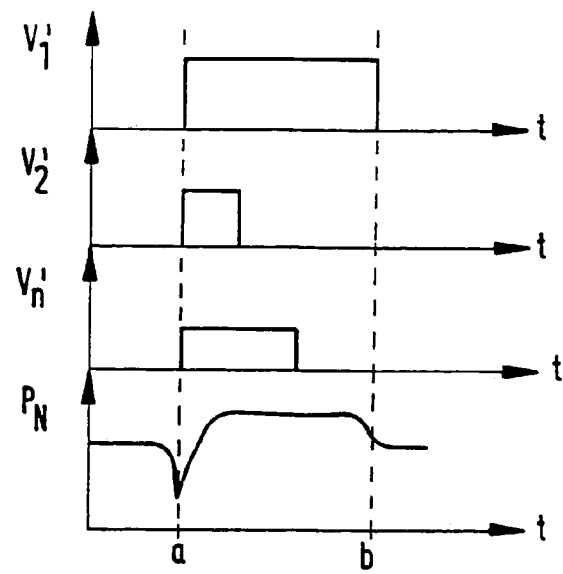
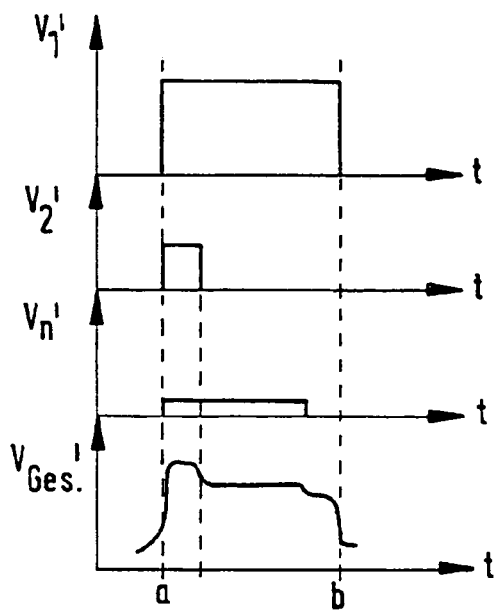
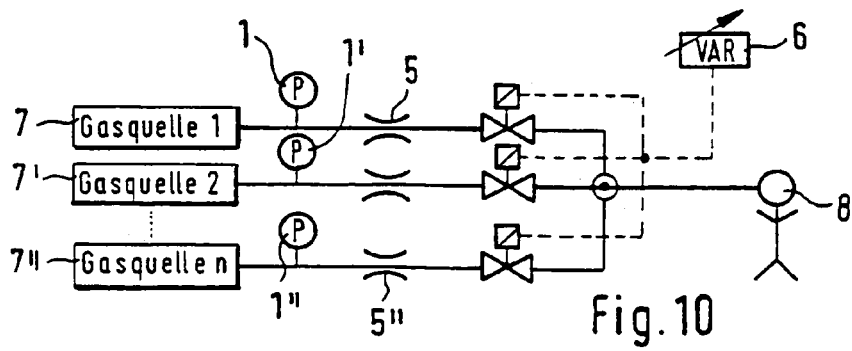

CONTROLLED GAS-SUPPLY SYSTEM

CROSS-REFERENCE TO RELATED APPLICATIONS

This application is a continuation-in-part of application Ser. No. 09/341,975, filed Aug. 26, 1999 now abandoned.

The invention relates to an apparatus for the controlled metering of gases, in particular for the controlled addition of NO or oxygen to a respiratory gas in apparatus for artificial respiration or respiratory donation.

Artificial respiration apparatus are used for mechanical artificial respiration, for anesthesia and for respiratory therapy by treatment with gases, e.g. oxygen donation or treatment with nitrogen monoxide (NO).

An inhalation-anesthesia apparatus is described, for example, in DE 37 12 598 A1. It is used to meter anesthetic gas into the respiratory gas.

DE 43 25 319 C1 describes an apparatus for continuously metering NO to the respiratory air of patients, containing a respirator, an NO metering vessel, a metering unit with control unit and an analyser for determining the NO concentration in the respiratory air. The control unit (monitoring and regulating unit) is responsible for metering the NO to be metered by determining the volumetric flow rates of respiratory gas and NO, taking into account the NO analysis parameter. The NO metering is proportional to volume or to volumetric flow rate, so that the NO concentration in the respiratory gas is always kept constant. The essential technical principles involved in metering NO in NO therapy are described in: "C. Krebs et al., Technological basis for NO application and environmental security, Acta Anaesthesiologica Scandinavica Supplement 109, Vol. 40, 1996; pp. 84-87".

Patients with chronic breathing difficulties (e.g. asthma and COPD (Chronic Obstructive Pulmonary Disease)) are assisted by a generally movable oxygen donor in the oxygen supply to the body. Such patients are referred to as spontaneously breathing patients, in contrast to patients who are connected to an artificial respiration apparatus by in-patient intubation. Thus, spontaneously breathing patients are given, for example, an additional oxygen donation (LOT=Long-term Oxygen Therapy) or respiratory assistance (via CPAP=Continuous Positive Airways Pressure). The gases are administered either via so-called nasal spectacles or a nasal probe (nasal application: in the most simple case, a gas supply tube, the opening of which is arranged to be open beneath the nasal orifice's of the patient) or by means of a breathing mask (particularly in the case of CPAP).

An apparatus for feeding respiratory gas or oxygen to a patient is described in DE 43 09 923 A1. A pulse-oxymeter is used to adapt the respiratory gas volume to be fed to the patient to the blood gas saturation level determined.

The invention is based on the object of providing an apparatus for supplying patients with one or more gases, the gas metering into a respiratory gas being individually adapted to a patient by means of a control unit of the apparatus.

The object is achieved by means of a program-controlled or a program- and sensor-controlled gas supply system, in particular by means of a gas supply system with controlled metering of at least one gas, in which system the gas is a pure gas or a gas mixture, the gas is metered in an inspiration-synchronized, Program-controlled and/or sensor-controlled manner, and the volume of gas metered in one respiratory cycle is dependent on the respiratory gas volume.

Gas supply systems are arrangements or devices which feed one or more gases to a patient or provide one or more gases to a patient for respiration. The gases, in particular medical gases, are preferably mixed with air, a respiratory gas or oxygen, so that gas mixtures which maintain respiration are obtained. A gas supply system is, for example, an artificial respiration system comprising artificial respiration apparatus and gas metering device for one or more gases. An artificial respiration system comprises, for example, hose connections or gas lines, gas source, gas metering device (gas metering unit), breathing mask, preferably a respiratory gas humidifier and, if appropriate, one or more gas filters (e.g. $NO_2$ filter). Artificial respiration systems having an artificial respiration apparatus are generally used for the in-patient treatment of patients. Gas-supply systems may be stationary or mobile, in particular portable, apparatus. Gas supply systems according to the invention are preferably used to treat humans or mammals with one or more gases, in particular for inhalation treatment of the lungs.

An artificial respiration system which, with modifications, can be used as a gas supply system is described, for example, in DE 43 25 319 C1, to which reference is made.

Gas supply systems are, for example, also gas-donating apparatus for spontaneously breathing patients. Such a gas supply system is described in DE 43 09 923 A1, to which reference is made.

The gas supply system generally contains a breathing mask or nasal spectacles. The gas supply system preferably contains a humidifier for the respiratory gas and/or gas.

The gas supply system preferably contains one or more gas sources. Gas sources are, for example, compressed-gas sources containing a compressed gas, such as compressed-gas vessels, compressed-gas cylinders, pressure boxes, compressed-gas lines or vessels containing cold-liquefied gas (e.g. for delivering evaporated, gaseous oxygen). A gas generator may also serve as a gas source. A gas generator is, for example, an on-site gas generator, e.g. for producing nitrogen monoxide (NO), in particular NO in nitrogen, by low discharge in a nitrogen/oxygen gas mixture. Further gas generators are, for example, electrolysis cells (e.g. for generating hydrogen) or chemical reactors (e.g. reaction chambers in which chemical reactions take place in order to generate gas). The gases are preferably medical gases. Medical gases are gases or gas mixtures which are used in the medical sector, for example for treating disorders; therapy, prophylaxis, anesthesia, diagnostics, improving the respiratory function or state of health of humans or mammals. Medical gases often have a pharmacological action. However, medical gases may also be used for other properties (e.g. as contrast agents for tomography, in particular NMR computer tomography of the lung or other image-generating procedures). Medical gases are, for example, oxygen, anesthetic gases such as laughing gas ($N_2O$) or xenon, hydrogen, noble gases such as helium, carbon dioxide ($CO_2$), nitrogen monoxide (NO) or gas mixtures containing one or more of the abovementioned gases as a constituent, e.g. helium/oxygen gas mixtures, helium/oxygen/NO gas mixtures or helium/oxygen/$CO_2$ gas mixtures. As an alternative to metering a gas mixture, the individual components or individual components and partial gas mixtures may also be metered in parallel (simultaneously or at different times) to, for example, a respiratory gas. Medical gases generally have a high purity.

The metering of one or more gases advantageously takes place only during inspiration phases. No gas metering takes place during expiration. Gas metering which is synchronized to the respiratory cycles is achieved by means of a trigger effect with the aid of a sensor. The start of inspiration or the start and end of inspiration is detected by a control unit on the basis of sensor measured values. Gas metering takes place continuously (e.g. with a fixed volume or concentration, of the metered gas per inspiration over the entire operating time) or discontinuously (e.g. with metering breaks), preferably a) program-controlled (e.g. time program), b) sensor-controlled, or c) with a combined program control and sensor control.

The control unit (e.g. microprocessor control, computer control) receives the measurement signal from the sensor for triggering the gas metering and preferably uses a program and/or sensor control to determine whether the gas is metered, and for what duration (pulse width $t_i$), at what volumetric flow rate $V_i'$ (differential change in the gas volume $V_i$ with respect to time t: $V_i'=dV_i/dt=$pulse height) and with what number $n_i$ of metering operations ($n_i$: number of pulses) the gas i is metered. This type of gas metering is referred to as pulse-modulated gas metering. The duration $t_{max}$, of inspiration and the beginning and end of inspiration are advantageously determined by means of a sensor. The pulse width $t_i$ is less than or equal to the duration $t_{max}$. The metered gas volume $V_i$ of a pulse is calculated on the basis of the equation $V_i=V_i'*t_i$, and the volume of gas metered during an inspiration is calculated on the basis of the equation $$V_i=V_i'*t_i*n_i.$$

The concentration $C_i$ of a metered gas, based on the respiratory gas volume $V_{ges}$ ($V_{ges}$=sum of all the gas volumes $V_i$), can be calculated, given $n_i=1$, according to the equation $$C_i=V_i/V_{ges}=V_i'*t_i/V_{ges}.$$

The values, of pulse width, pulse height and number of pulses within one inspiration may be fixed in advance or variable.

In many applications, a gas is advantageously metered by the combination of a basic metering, preferably with constant settings for $V_i'$, $n_i$ and $t_i$, and an additive metering with variable (controlled) settings of $V_i'$, $n_i$ and $t_i$. Basic metering and additive metering of a gas are preferably carried out using separate metering devices (e.g. controlled solenoid valves). The basic metering may in this case provide a basic supply of a gas and the gas volume and gas concentration are regulated by the additive gas metering. In this case, the additive gas metering may be program- or sensor-controlled.

Measured values from the preceding inspiration, e.g. the duration of inspiration ($t_{max}$) and/or the respiratory gas volume ($V_{ges}$), are used to control the metering of a gas. Controlled variables are, for example, the gas concentration $C_i$ or the mixing ratio of gases (e.g. $V_1/V_2$).

By means of a program, the gas metering can be varied between a lower limit value and an upper limit value, e.g. the gas concentration can be increased and reduced over a series of inspirations (e.g. in a regular sequence with an even or uneven ratio of raising and lowering the gas concentration; advantageous for NO metering). The gas metering may also advantageously be controlled on the basis of a response curve previously determined on the patient. To determine the response curve, a sensor is used to measure a body parameter of the patient (e.g. oxygen saturation in the peripheral blood and/or heart rate, determined by means of pulse-oximeter) as a function of the metered volume of gas or gas concentration, and the temporal gas demand required to establish a uniform body condition is determined.

In a further process variant of the gas metering, the sequence of the program used to control the metering of a gas is dependent on certain measured variables, which are detected by one or more sensors, being reached. For example, if a measured variable falls below or exceeds a threshold; program sequences of the gas metering may be triggered. One threshold may activate a program section which brings about a metering sequence for high, average or low gas metering.

The gas metering is advantageously a metered addition of the gas (e.g. oxygen or NO or NO-containing gas) to the respiratory gas in metering intervals of a defined sequence (sequential gas metering). Thus, the gas metering is carried out, for example, via a repeating sequence of inspiration cycles with gas metered to the respiratory gas (gas metering) and inspiration cycles without gas being added (exclusion).

The sequential gas metering is, for example, a repetition of the following sequences (regular sequences) with an equal duration of the metering intervals (e.g. metered addition of oxygen or NO during artificial respiration or for spontaneously breathing patients):

a) one metered gas addition and one exclusion, b) 2 metered gas additions (e.g. 2 inspiration phases with metered gas addition) and 25 following exclusions (i.e. 25 following inspiration phases without metered gas addition), c) 10 metered gas additions and 30 following exclusions, or d) 3 metered gas additions and 80 following exclusions.

A metered gas addition may also comprise variable (irregular) sequences, e.g. a succession of sequences with increasing or decreasing numbers of metered gas additions.

The most simple sequence is the sequence comprising one metered gas addition and one exclusion. The repetition of the sequence provides the overall cycle of metering steps (of gas metering). Examples of different forms of sequential gas metering are listed in the table.

TABLE

Forms of sequential gas metering (where $n_i = 1$)

| Type of metering | Gas concentration or gas volume in the metering interval | Duration of the metering interval | Sequence of the metering intervals |
|---|---|---|---|
| 1. | Constant | Constant | Constant |
| 2. | Constant | Constant | Variable |
| 3. | Constant | Variable | Constant |
| 4. | Constant | Variable | Variable |
| 5. | Variable | Variable | Constant |
| 6. | Variable | Constant | Variable |
| 7. | Variable | Constant | Constant |
| 8. | Variable | Variable | variable |

The sequential gas metering has the advantage that for a time high levels of gas can be metered, while nevertheless on average, over a period of time, a very low concentration or volume of gas is added. For example, a sequence of one or more (two, three, four, five, six, seven, eight, nine, ten or more) inspirations can be used to administer a standard NO dose (e.g. up to 80 ppm NO in the respiratory gas for extremely severe pulmonary failure), and then a sequence of inspirations (one, two, three, four, five, six, seven, eight, nine, ten or twenty, thirty, forty, fifty or more inspirations) can be used to administer a very low quantity of NO, so that the result is an average NO concentration which lies, for example, in the ppb or ppt range. The sequential gas metering of two, three or more gases can be combined.

The controlled gas metering leads to a lower consumption of gas, in particular to a lower overall volume of gas administered, so that side-effects from the gas (e.g. NO) on the patient can be reduced. A further advantage is that discontinuation and withdrawal of the gas therapy (e.g. NO therapy) are made easier. It is generally advantageous when withdrawing artificially respirated patients who need NO to continuously reduce the amount of NO administered. When using an artificial respiration system with controlled NO metering, a further significant advantage is that the level of toxic $NO_2$ formed overall from NO in the artificial respiration is lower.

Control equipment for gas metering can advantageously be controlled electrically. Control equipment used is, for example, time- and/or sensor-controlled solenoid valves (e.g. solenoid valve with upstream-connected electronics, sold by Bürkert, Germany), mass throughput regulators (e.g. appliance type MFC from Brooks, the Netherlands), automatically adjustable pressure regulators (e.g. adjustable by means of stepper motor or electric motor) or control valves for the direct, in particular automatic, adjustment of the gas pressure. In the case of gas sources containing cold-liquefied gas, the evaporation of the gas is advantageously regulated by means of a heating device in the storage vessel. The heating device is preferably an electrical resistance heater which is controlled by switching the heating current on or off or by continuously, varying the heating output. In addition, the gas can be metered by means of a solenoid valve in the gas supply line.

Sensors are generally measurement sensors. The term also comprises (in a broad sense) measurement appliances and analysis devices. The use of sensors can be divided into sensors for triggering the gas metering (trigger sensors), sensors for controlling the sequence of gas metering (regulating sensors) and sensors for monitoring the safety of the gas supply system (e.g. for triggering an alarm or for safety shut-off of apparatus functions, in particular by means of gas sensors).

A suitable trigger sensor is a pressure sensor which measures the gas pressure, in particular a low-pressure sensor. The measured signal from the sensor can itself be used as a control signal (e.g. in the case of a so-called "smart sensor") or can be converted into a control signal by means of an electronic processing and control unit. The sensor may, for example, measure the pressure (gas pressure) in or in front of the nose (e.g. by means of a sensor which is integrated in the breathing mask or nasal spectacles). A pressure sensor is also suitable for detecting the profile of the Inspirational reduced pressure and can be used to control a gas metering which is adapted to requirements (e.g. higher gas metering for deep inspirations, lower gas metering for shallow inspiration). It is also possible to measure differential pressures and use these for control purposes (e.g. differential pressure with respect to pressure at corresponding phase of preceding inspiration), since at a defined setting these pressures indicate the square of the flow rate.

Regulating sensors are, for example, pressure sensors, gas-specific sensors or gas sensors (e.g. electrochemical gas sensors for $O_2$, NO or $NO_2$) and, in particular, sensors for detecting physical reactions, body functions or body states of the patient (patient-oriented measured values), sensors for measuring the oxygen saturation in the peripheral blood, e.g. pulse-oxymeters (e.g. ASAT appliance from Baxter, USA), sensors for blood gas analysis (e.g. 995 HO appliance from AVL, Austria; "Perotrend" appliance from Crosstec), sensors for measuring blood pressure or sensors for measuring pulmonary blood pressure (also pulmonary pressure or pulmonary artery pressure; by means of a catheter floating in the pulmonary artery, e.g. type SWAN-Ganz from Baxter, USA, with electrical conversion by means of the "Explorer" appliance from Baxter), sensors for measuring the cardiac output or cardiac rate or sensors for detecting artificial respiration parameters, such as artificial respiration pressure, artificial respiration volume or compliance (expansibility of the lung).

Heart rate and oxygen saturation in the peripheral blood can be measured by means of pulse-oxymeters. The simultaneous detection of both parameters is advantageously used to control the gas metering, e.g. when metering oxygen and/or NO in artificial respiration systems or systems for spontaneously breathing patients, in particular in the gas therapy of COPD patients.

Preferably, highly miniaturized sensors (in particular pressure sensors), which allow positioning directly at the measurement site (e.g. on the nose, on or in the patient's body) are used. However, the sensor may also be arranged at a distance from the actual measurement site, e.g. may be positioned in the metering line, or may be connected to the measurement site by means of a suitable hose line. This may, for example, be the case when vacuum measurement apparatus (pressure measuring apparatus) are used as sensors or in the case of sensors (measurement apparatus, analysis apparatus) for determining the concentration of a gas component, e.g. NO concentration, carbon dioxide concentration or oxygen concentration. It is also possible to combine different sensors in order to control the gas metering and/or gas mixture. For example, it is possible to use a combination of pressure sensors and gas sensors.

The use of the sensors allows automatic, patient-oriented gas metering.

The invention is explained below on the basis of NO metering, oxygen therapy and the combined metering of NO-containing gas and oxygen.

The NO metering is advantageously controlled using a curve indicating the response of the patient to NO. The response curve of the patient is determined in advance, i.e. the temporal dependence of a measured variable (a Parameter) on the quantity or concentration of NO administered. The response curve may, for example, be determined by measuring the increasing oxygen content in the peripheral blood which is brought about by the NO metering and/or by the pulmonary pressure, which falls during NO metering. This response curve can be used to determine the most suitable NO metering. An empirically determined set value can be compared with the measured variable in order to control the NO metering and, on this basis, a control unit (e.g. flow regulator or solenoid valve) can be actuated, the NO quantity, for example, being controlled in such a way that the temporal change in the measured variable measured on-line comes closer to the response curve.

Limit values for the NO concentration to be set (minimum, maximum concentration), number of respiratory cycles with and without metered addition and optimum, parameters for controlling the gas metering can be determined in a preceding determination or during the therapy itself (determination of the control parameters: desired gas concentration profile over the course of time). The following procedure can be used to optimize the NO metering (automatic detection and adaptation of the most favorable (minimum required) NO quantity):

1. Constant increase in quantity of NO (NO increase) from lower limit (e.g. 0.1 ppm NO) to upper limit (e.g. 100 ppm), involving measuring the oxygen saturation in the peripheral blood and/or the pulmonary pressure (observing the reaction of the patient=response). Determining the appropriate NO concentration (becomes set value for control). Monitoring the set value by means of second response measurement (passing through the NO concentration lower limit/upper limit/lower limit=triangular measurement). The optimum NO profile (NO concentration curve in the respiratory gas) is achieved when a constant oxygen saturation in the peripheral blood or a minimum, constant pulmonary pressure is established (adaptive control of gas metering).

The gas supply system is used, for example, in the treatment of hypoxia or high lung pressure with NO. It is also advantageously used for the following disorders/clinical pictures: ARDS (Adult Respiratory Distress Syndrome), asthma, PPH (Primary Pulmonary Hypertension), COPD (Chronic Obstructive Pulmonary Disorder), heart malformation, immature lungs in the case of premature and newborn infants.

In the case of gas supply systems for oxygen therapy, it is advantageous to use the measurement of the oxygen saturation of hemoglobin in the peripheral blood (e.g. measurement by means of a pulse-oxymeter). The oxygen concentration in the respiratory gas or the oxygen volume is controlled. The control range of the oxygen concentration extends to up to 100% by volume.

In the same way as for the NO metered addition, in this procedure for which the gas supply system is being used the metered addition of oxygen is regulated in a controlled manner.

In oxygen therapy, discontinuous measurement methods for determining the oxygenation in the circulation can be used as measured and regulating variables, e.g. by means of the HO 995 apparatus from AVL (Austria), or alternatively continuous measurement methods, e.g. using the "Perotrend" appliance from Crosstec, can be used. Blood gas analysis generally determines arterial blood gas, venous blood gas or mixed-venous blood gas.

The gas supply system for automatic oxygen metering in oxygen therapy is advantageously suitable for use in both spontaneously breathing and artificially respirated patients. In particular, pulse-modulated metering of oxygen or other additional gases is advantageously controlled on the basis of measured variables such as blood oxygen content and/or pulmonary blood pressure or blood oxygen content and/or heart rate.

Program control for the oxygen metering and, if appropriate, further metered gases allows a gas supply system to have a particularly simple design, in particular to be a portable gas supply system for chronically ill patients (e.g. COPD patients).

The gas supply system is particularly advantageously suited to controlled, adapted gas metering of two or more gases, e.g. selected from the gases NO, oxygen, hydrogen gas, helium and carbon dioxide. The controlled metering of helium is used to improve the airing of the lungs, while carbon dioxide stimulates respiration. A sensor control system and/or a program control system may be provided for each gas. Two or more gases can be metered on the basis of the determination of overall volumetric flow rate or partial volumetric flow rates of the individual gases. In principle, the gases can be metered in the same way as one individual gas is metered. A mutually adapted metering of the gases is preferred. For example, the gas mixing ratio may be selected as a control parameter. When metering a plurality of gases, it is, of course, possible to use different control types for the individual gases, e.g. to control some of the gases using a sensor control unit and some using a program control unit or some using a combined program/sensor control unit. By suitably selecting one or more gas sources (e.g. liquid oxygen, NO-containing gas, in particular NO-containing gas from an on-site generator) and providing a suitable control unit, the power required to operate the gas supply system can be considerably reduced (advantageous for battery-operated mobile systems).

For pulse-modulated gas metering, in particular for metering two or more gases, it is important for the respiratory gas to be as homogeneously mixed as possible, in order to avoid concentration peaks of a gas in the respiratory gas. It is advantageous to homogenize the gas mixture by means of a mixing body in the hose system, preferably in the respiratory tube. Preferably, a hollow-cylindrical part which has a helically twisted part (e.g. metal strip or plastic strip with ends rotated through 180° with respect to one another) is fitted in the tube system as the mixing body.

The mixing path is both for tube systems used in the intensive care sector (22 mm tube diameter for artificial respiration Of adults, 15 mm for children, 10 mm for newborn infants) and, for example, for 8 mm or 10 mm tube systems for home therapy of the chronically ill, in particular COPD patients.

Filters, absorbers or humidifiers, e.g. in a respiratory tube, also improve the homogenous mixing of gases Use on patients for NO application, e.g. for the chronically ill, is improved by fitting a filter for nitrogen dioxide ($NO_2$), e.g. filters containing polyphenylene sulfide as filter material or sodium carbonate cartridges (Sodalime). It is also advantageously possible to combine an on-site generator for NO with a $NO_2$ filter.

The following figures explain the invention and describe gas supply systems for spontaneously breathing patients (e.g. COPD patients).

FIG. 1 diagrammatically shows a breathing mask 2 with sensor 1 (e.g. pressure sensor) and gas supply tube 3 (e.g. oxygen) as parts of a gas supply system.

FIG. 2 diagrammatically shows nasal spectacles 4 with sensor 1 (e.g. pressure sensor) and gas supply tube 3 (e.g. oxygen). A plurality of nasal spectacles 4 may be arranged on the patient in order to supply the patient with different gases. As an alternative to a plurality of nasal spectacles, it is also possible to use coaxial tubes, in which a different gas flows through each lumen.

Figure 1:
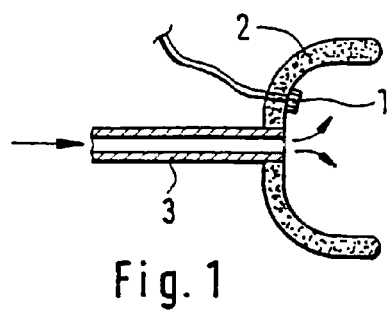
Figure 2:
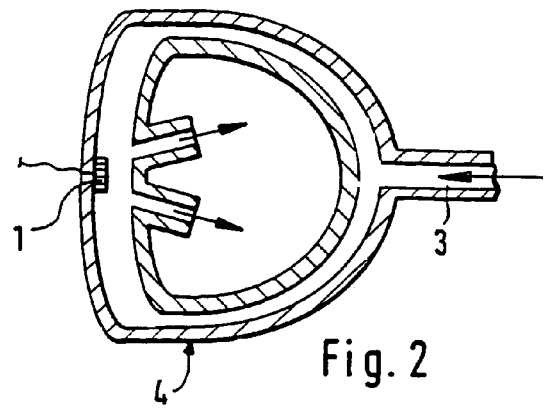
Figure 3:
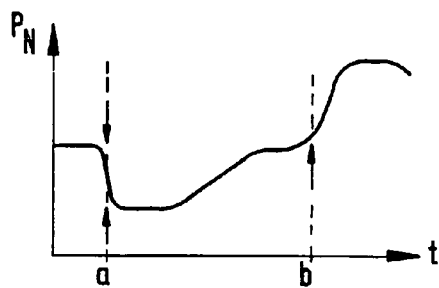
FIG. 3 shows a schematic diagram of the nasal pressure $P_N$ as a function, of time t without gas metering, measured by means of a pressure sensor in front of the nasal orifice. The marks a and b indicate the start and end of an inspiration interval.
Figure 4:
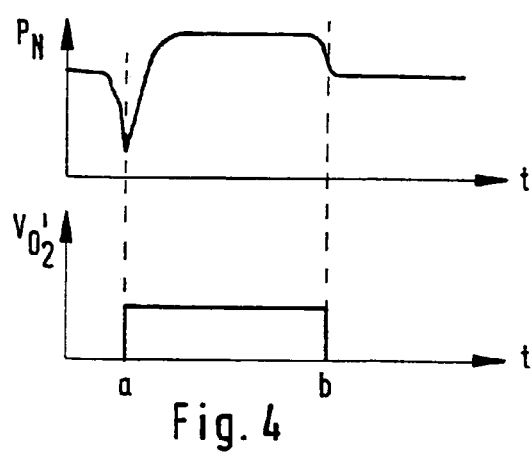
FIG. 4 shows a schematic diagram of the measured nasal pressure $P_N$ as a function of time t when metering oxygen. The bottom diagram (figure) shows the Volumetric flow rate of metered oxygen in the metering interval a to b (inspiration interval).
Figure 5:
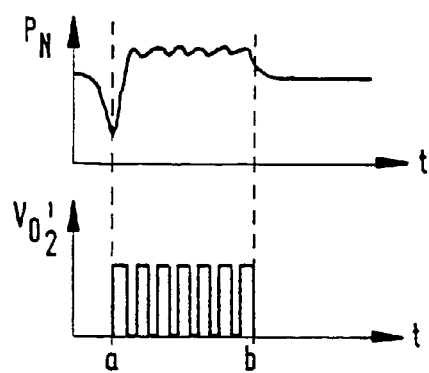
FIG. 5 shows a schematic diagram of the measured nasal pressure $P_N$ as a function of time t with pulsed metering of oxygen. The bottom diagram (figure) shows the volumetric flow rate of pulsed, metered oxygen in the metering interval a to b (inspiration interval).
Figure 6:
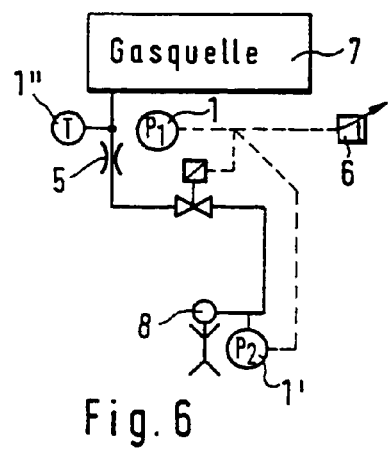

FIG. 6 diagrammatically shows a sensor-controlled gas supply system with a plurality of sensors 1 (P1: pressure), 1' (P2: pressure) and 1" (T: temperature) and a gas source 7 (e.g. oxygen). If the pressure of the gas (e.g. oxygen) is known either from a on-off or a continuous measurement of the pressure (P1) and of the diameter of one or possibly more nozzles 5 or constrictions (may also, for example, be the diameter of the valve inlet or valve seat), it is thus possible to determine on a on-off or continuous basis the volumetric flow administered to the patient and, if the duration is known, to determine the volume of gas administered. It is also possible; by means of the temperature (temperature sensor), to determine the volumetric flow rate by means of a pressure/temperature back-calculation for the precise standard volumetric flow rate. The trigger of the start of the inspiration phase and hence the beginning of opening of the solenoid valve can be triggered by the low-pressure sensor P2. The duration of opening and therefore the volume to be administered is displayed or adjusted by means of a volume assigned to a potentiometer on the control unit 6 (or by input/display of a more highly electronicized system, such as for example Microprocessor/controller).

FIG. 7 diagrammatically shows a gas supply system with pressure-reducing device at the gas source 7. By varying the pressure of the supply gas, this may be a compressed-gas vessel with pressure-reducing device or a liquefied-gas vessel with evaporation device, with or without pressure-reducing device, the volumetric flow rate can be altered. This is detected by means of the pressure measurement and the new time or the new volume administered can be displayed and calculated/controlled.

FIG. 8 diagrammatically shows the profile of the total volumetric flow rate analogously to the nasal pressure $P_N$ (bottom diagram) when metering a plurality of gases with the respective volumetric flow rates $V_1$, $V_2$, $V_n$. A suitable gas supply system is shown in FIG. 11.

Analogously to FIG. 8, FIG. 9 shows the profile of volumetric flow rates produced for various gases. FIGS. 8 and 9 are examples of different mixing ratios produced for a plurality of gases.

FIG. 10 diagrammatically shows a gas supply system with a plurality of gas sources 7, 7' and 7" and assigned pressure sensors 1, 1' and 1".

Figure 11:
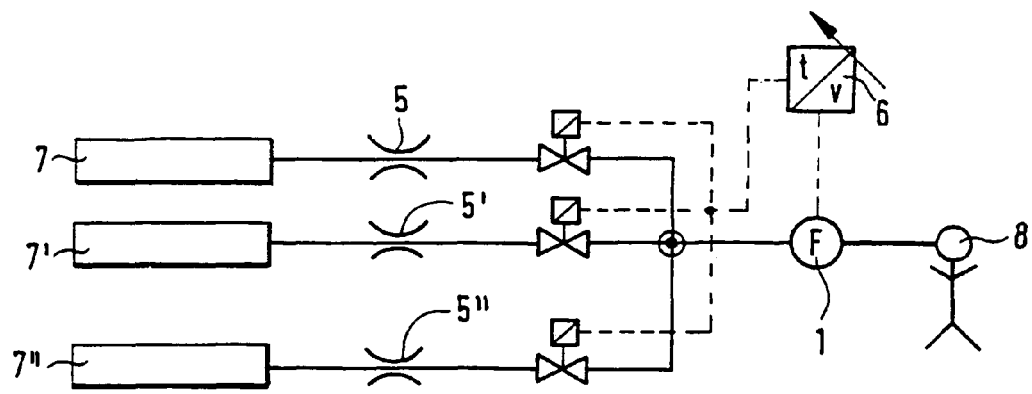

FIG. 11 diagrammatically shows a gas metering system with a plurality of gas sources 7, 7' and 7" and associated pressure-reducing devices (e.g. nozzles) 5, 5' and 5" and a sensor 1 for controlling the solenoid valves by means of a control unit 6.

Figure 12:
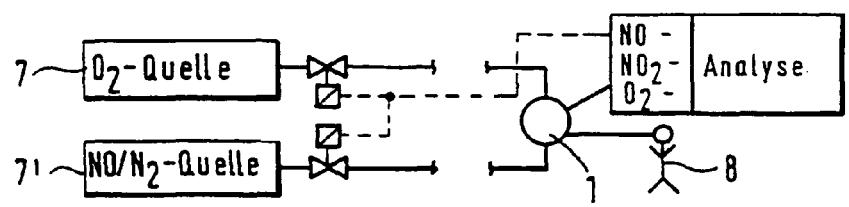

FIG. 12 shows the delivery of gas from the gas sources 7 (e.g. oxygen) and 7' (e.g. NO source) via a sensor 1 and/or a gas analysis unit.

Figure 13:
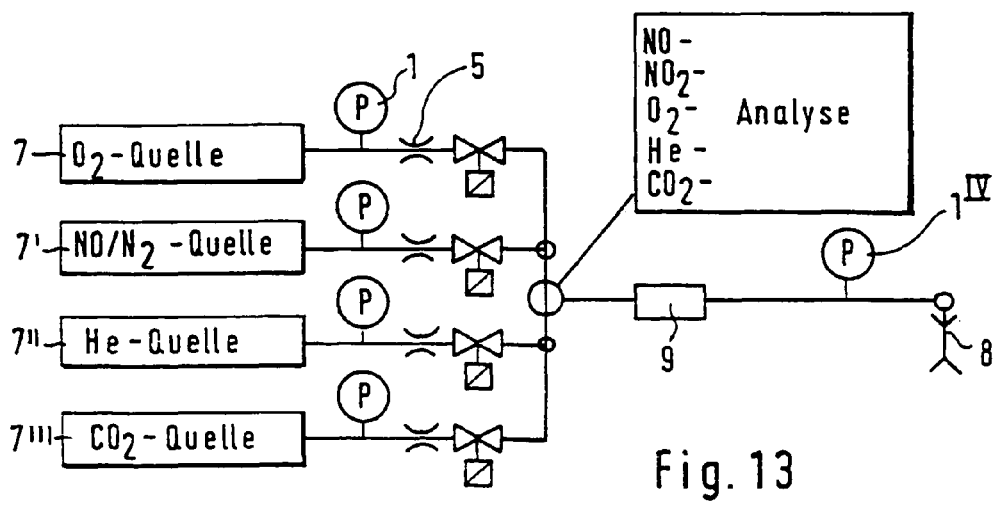

FIG. 13 shows a gas supply system with a plurality of gas sources 7 to 7''' (e.g. oxygen, NO source, helium, carbon dioxide) using sensors 1 to 1''' and patient-mounted sensor 1$^{IV}$ and filter element 9.

Figure 14:
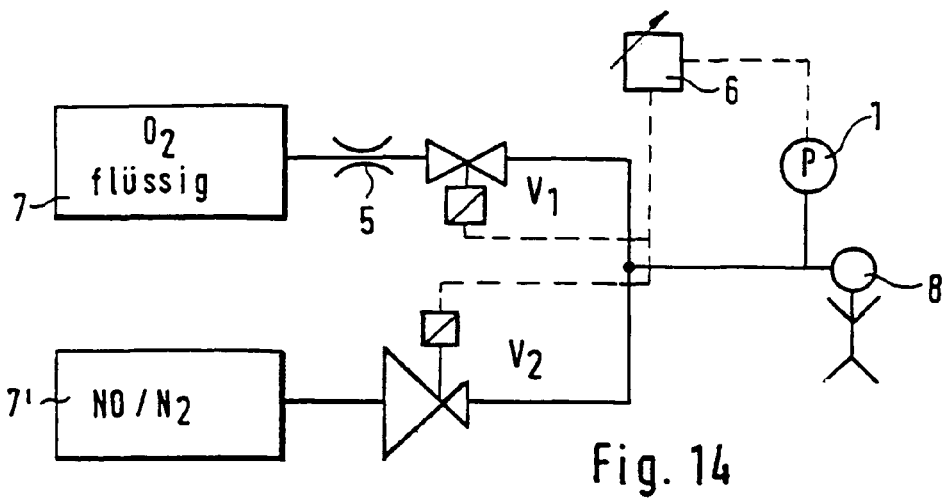

FIG. 14 diagrammatically shows a gas supply system for liquid oxygen and NO-containing gas. The valves V1 and V2 (e.g. solenoid valves) are controlled by means of the patient-mounted sensor 1 (e.g. pressure sensor) in conjunction with the control unit 6.

Figure 15:
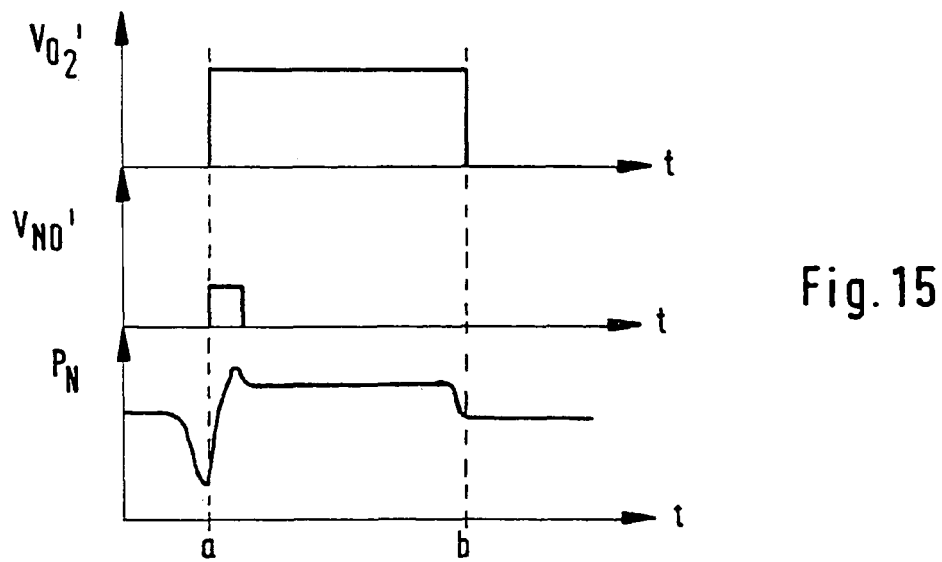

FIG. 15 diagrammatically shows the temporal profile of volumetric flow rates of oxygen and NO-containing gas and of the measured nasal pressure $P_N$.

Figure 16:
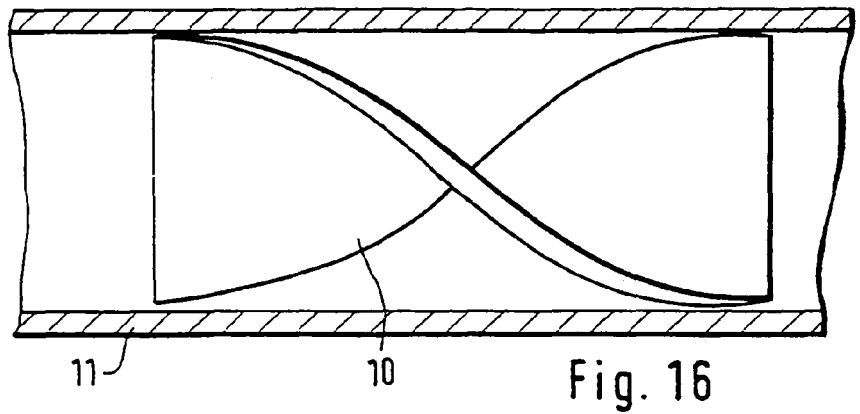

FIG. 16 shows a mixing device for gases, comprising hollow-cylindrical part 11 and mixing body 10, which is formed a twisted flat body (e.g. made from metal, plastic or glass; ends of the flat body rotated with respect to one another, e.g. 180° or 360°). The mixing device, as mixing path, is preferably fitted in the respiratory tube of the gas supply system.

EXAMPLE

NO Metering as a Function of Oxygen Volume

A portable unit for the combined metering of oxygen and NO (in nitrogen) contains a storage vessel for cold-liquefied oxygen with integrated evaporation system (capacity: 0.5 liters), a compressed-gas vessel for NO-nitrogen gas mixture (typically 800 to 1000 ppm NO in $N_2$; geometric cylinder volume: 0.2 to 1.0 liter; filling pressure: 150 to 200 bar), a control unit for controlling the metering of oxygen and NO gas mixture, at least 2 electrically controllable solenoid valves, gas hoses and nasal spectacles with pressure sensor, NO sensor and $NO_2$ sensor in the respiratory gas line, a warning system and safety device (alarm: when NO gas mixture cylinder empty, when oxygen storage vessel empty, excessive oxygen, NO or $NO_2$ concentration in the respiratory gas).

The pressure sensor is used to trigger the gas metering (inspiration-synchronized gas metering). At the start of inspiration, the solenoid valve for oxygen metering and the solenoid valve for NO gas mixture metering are opened. The volume of oxygen metered per inspiration is preset, e.g. $V_{O2}$=50 ml. A set oxygen volumetric flow rate $V_{O2}'$ of 3000 ml/minute results in a pulse width $t_{O2}$ of 1 second. The NO concentration to be set in the respiratory gas volume $V_{ges}$ ($V_{ges}=V_{O2}+V_{NO}$) is to amount to $C_{NO}$=35 ppm. The NO gas mixture contains 1000 ppm NO. The preset NO gas mixture volumetric flow rate $V_{NO}'$ amounts to 500 ml/minute. The metered volume of NO gas mixture $V_{NO}$ required to set the NO concentration $C_{NO}$=35 ppm (volume/volume) in the respiratory gas is calculated as follows:

$$C_{NO}=(V_{NO}*F)/V_{ges}=(V_{NO}*F)/(V_{O2}+V_{NO})$$

where F: NO concentration in the NO gas mixture. It follows that $V_{NO}=(V_{O2}*C_{NO})/(F-C_{NO})$.

Where $V_{O2}$=3000 ml, $C_{NO}$=35 (ppm) and F=1000 (Ppm), $V_{NO}$=1.8 ml.

The opening time of the NO metering valve (in this function open/shut function) is fixed by $V_{NO}=V_{NO}'*t_{NO}$. The opening time of the solenoid valve for NO gas mixture metering is therefore 218 milliseconds (where $V_{NO}'$=500 ml/minute). For reasons of homogeneity, it is advantageous for the metering conditions to be selected in such a way that the NO metering time is $t_{NO}=½\ t_{O2}$. This is achieved by reducing the volumetric flow rate $V_{NO}'$ by lowering the preliminary pressure in the gas metering line. The preliminary gas pressure is advantageously reduced by means of a controllable diaphragm or nozzle incorporated in the gas metering line (automatic adjustment of the diaphragm aperture or nozzle aperture).

In order to simplify illustration, the calculation example contains only one predetermined NO concentration. It is preferable for the NO concentration to be varied by means of a control program or a sensor control system:

One of the characteristics of the various methods of this invention where, for example, at least one respiratory gas is supplied during only the inspiration cycles of the patient are that the characteristics of the gas pulses during a predetermined plurality of repetitive sequences of inspiration cycles are defined whereby the pulse length, pulse height and pulsing frequency for each individual inspiration cycle in the sequences is so defined. For some sequences the characteristics of the gas pulses are varied within some of those sequences without requiring the gas pulses characteristics to be the same for all sequence and independently of the exhaled gas and of the breathing gas.

Where the method is used for supplying at least one additive gas into the respiratory gas then similarly the pulse length, pulse height and pulsing frequency for each individual inspiration cycle in the sequences is defined and sometimes the characteristics of the gas pulses within the sequences are varied without requiring the gas pulses characteristics to be the same for all sequences and independently of the exhaled gas and of the breathing rate.

The invention claimed is:

1. A method of sequential metering one or more medical gases to a human or mammal patient with a sensor exposed to the respiration and a control unit, metering the medical gas only during the inspiration cycles of the patient, whereby the medical gas metering is carried out via a repeating sequence of inspiration cycles with medical gas metered to the breathing gas (gas metering) during some of the inspiration cycles and during other inspiration cycles without medical gas being added (exclusion) and independently of the exhaled gas and of the breathing rate, with consecutive sequences thereby not requiring identical mixtures of breathing gas and added metered medical gas, and supplying the breathing gas with any added metered medical gas to the patient.

2. A method according to claim 1, including following each sequence by an identical sequence until the control components change the characteristics of the gas pulses for the next sequence.

3. A method according to claim 1, including supplying more than one gas to the patient and the characteristics of the gas pulses from the different gases differ from each other.

4. A method according to claim 1, wherein at least one sequence differs from at least one other sequence in a pattern of sequences wherein in at least one inspiration cycle there is gas metering followed by at least one inspiration cycle of exclusion, and further inspiration cycles include a pattern of gas metering in some inspiration cycles and exclusion in other inspiration cycles.

5. A method according to claim 1, including controlling the amount and duration of the respiratory gas being metered by a control unit selected from the group consisting of (a) a program control unit, (b) a sensor control unit and C) a combined program/sensor control unit, and metering the additive gas in a manner selected from the group consisting of a pulse-modulated manner and an in sequences manner.

6. A method according to claim 5, wherein the control unit includes a program unit having a program, using a sequence of the program for controlling the metering of the gas where the sequence of the program is dependent on a measured variable being reached, and triggering program sequences of the gas metering in the event of a threshold of a measured variable being exceeded or undershot.

7. A method according to claim 5, including using measured values from a previous breath to control the metering of the gas.

8. A method according to claim 5, carrying out the gas metering by a first metering with constant settings and an additional metering from the control unit.

9. A method according to claim 1, wherein the medical gas is nitric oxide.

10. A method of pulse-modulated metering one or more medical gases to a human or mammal patient with a sensor exposed to the respiration and a control unit, whereby the control unit receives the measurement signal from the sensor for triggering the medical gas metering and uses a program and/or a sensor control to determine whether the medical gas is metered and for what duration, and/or with what number of metering operations the gas is metered, metering the medical gas as an additive to the respiratory gas only during the inspiration cycles of the patient and independently of the exhaled gas and of the breathing rate, and supplying the respiratory gas with any additive metered medical gas to the patient, and wherein the medical gas is omitted from some of the sequences.

11. A method according to claim 10, wherein the characteristics of the gas pulses of the respiratory gas during a predetermined sequence of inspiration cycles is defined by the pulse length, pulse height and pulsing frequency for each individual inspiration cycle in the predetermined sequence.

12. A method according to claim 10, including supplying more than one medical gas to the patient and the characteristics of the gas pulses from the different gases differ from each other.

13. A method according to claim 10, including supplying an additive medical gas selected from the group consisting of nitric oxide, xenon, helium, oxygen, nitrous oxide, hydrogen and carbon dioxide.

14. A method according to claim 10, wherein at least one sequence differs from at least one other sequence.

15. A method according to claim 10, wherein only one additive medical gas is supplied.

16. A method according to claim 10, wherein a plurality of additive medical gases are supplied.

17. A method according to claim 16, wherein the additive medical gases are oxygen and nitric oxide.

18. A method according to claim 10, including metering the additive medical gas by controlling the amount and duration of the additive medical gas by a control unit selected from the group consisting of (a) a program control unit, (b) a sensor control unit and C) a combined program/sensor control unit, and metering the additive medical gas in a manner selected from the group consisting of a pulse-modulated manner and an in sequences manner.

19. A method according to claim 18, wherein the control unit includes a program unit having a program, using a sequence of the program for controlling the metering of the additive medical gas where the sequence of the program is dependent on a measured variable being reached, and triggering program sequences of the gas metering in the event of a threshold of a measured variable being exceeded or undershot.

20. A method according to claim 18, including using measured values from a previous breath to control the metering of the additive medical gas.

21. A method according to claim 18, including carrying out the additive medical gas metering by a metering with constant settings and by an additional metering from the control unit.

22. A method of sequential metering one or more medical gases comprising nitric oxide to a human or mammal patient with a sensor exposed to the respiration and a control unit, metering the medical gas only during the inspiration cycles of the patient, whereby the medical gas metering is carried out via a repeating sequence of inspiration cycles with medical gas metered to the breathing gas (gas metering) during some of the inspiration cycles and during other inspiration cycles without medical gas being added (exclusion) and independently of the exhaled gas and of the breathing rate, with consecutive sequences thereby not requiring identical mixtures of breathing gas and added metered medical gas, and supplying the breathing gas with any added metered medical gas to the patient.

* * * * *